United States Patent
Ma et al.

(10) Patent No.: US 8,079,957 B2
(45) Date of Patent: Dec. 20, 2011

(54) SYNCHRONIZED THREE OR FOUR-DIMENSIONAL MEDICAL ULTRASOUND IMAGING AND MEASUREMENTS

(75) Inventors: Qinglin Ma, Bellevue, WA (US); Gianluca Paladini, Skillman, NJ (US); Wei Li, East Brunswick, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1209 days.

(21) Appl. No.: 11/283,436

(22) Filed: Nov. 18, 2005

(65) Prior Publication Data
US 2007/0129631 A1 Jun. 7, 2007

(51) Int. Cl.
*A61B 8/00* (2006.01)
(52) U.S. Cl. .......................... 600/438; 600/437
(58) Field of Classification Search .................. 600/407, 600/437, 438, 440, 441, 443, 447, 449, 450
See application file for complete search history.

(56) References Cited

U.S. PATENT DOCUMENTS

| | | | | |
|---|---|---|---|---|
| 3,744,479 A | * | 7/1973 | Stein et al. | 600/440 |
| 5,282,471 A | * | 2/1994 | Sato | 600/443 |
| 5,611,025 A | | 3/1997 | Lorensen et al. | |
| 5,724,974 A | | 3/1998 | Goodsell, Jr. et al. | |
| 5,743,266 A | * | 4/1998 | Levene et al. | 600/458 |
| 5,782,762 A | | 7/1998 | Vining | |
| 5,920,319 A | | 7/1999 | Vining et al. | |
| 5,957,138 A | * | 9/1999 | Lin et al. | 600/453 |
| 6,083,162 A | | 7/2000 | Vining | |
| 6,272,366 B1 | | 8/2001 | Vining | |
| 6,366,800 B1 | | 4/2002 | Vining et al. | |
| 6,447,453 B1 | * | 9/2002 | Roundhill et al. | 600/443 |
| 6,606,091 B2 | | 8/2003 | Liang et al. | |
| 6,641,537 B2 | | 11/2003 | Morris et al. | |
| 6,694,163 B1 | | 2/2004 | Vining | |
| 6,771,262 B2 | | 8/2004 | Krishnan | |
| 2003/0152897 A1 | | 8/2003 | Geiger | |
| 2005/0213837 A1 | | 9/2005 | Boykov et al. | |

OTHER PUBLICATIONS

Jensen, Jorgen A. Estimation of Blood Velocities Using Ultrasound: A Signal Processing Approach. Cambridge: Cambridge University Press, 1996: 10-15.*
"Virtual Angioscopic Visualization and Analysis of Coronary Aneurysms Using Intravascular Ultrasound Images," by Tina A.A. Ayeni, et al.; Biomedical Imaging Resource, Mayo Foundation, 9 pages. (2001).
"Virtual Endoscopy Using Perspective Volume-Rendered Three-Dimensional Sonographic Data: Technique and Clinical Applications," Esther L. Yuh, et al.; AJR:172, May 1999 (pp. 1193-1197).
U.S. Appl. No. 11/098,676, filed Apr. 4, 2005.
U.S. Appl. No. 11/217,211, filed Aug. 31, 2005.
U.S. Appl. No. 11/230,598, filed Sep. 20, 2005.
U.S. Appl. No. 11/234,965, filed Sep. 26, 2005.
U.S. Appl. No. 11/241,603, filed Sep. 29, 2005.

* cited by examiner

*Primary Examiner* — Tse Chen
*Assistant Examiner* — Peter Luong

(57) ABSTRACT

Ultrasound imaging is synchronized with measurements. Generating three-dimensional representations is synchronized with measuring one or more parameters. For example, measurements are preformed based on navigating through a volume. The measurements are linked to the corresponding three-dimensional representations. As another example, the user selects a measurement from a graph. A three-dimensional representation of the volume associated with the selected measurement is presented.

19 Claims, 3 Drawing Sheets

SYNCHRONIZED THREE OR FOUR-DIMENSIONAL MEDICAL ULTRASOUND IMAGING AND MEASUREMENTS

BACKGROUND

The present embodiments relate to three-dimensional (3D) or four-dimensional (4D) imaging. In particular, measurements are provided for 3D or 4D imaging.

3D and 4D ultrasound imaging may show a baby face to the parents or provide medical diagnostic information. Two-dimensional or matrix arrays allowing real-time 3D (i.e., 4D) imaging provide diagnostic information for cardiologists. One alternative is to use one-dimensional arrays, slices of two-dimensional (2D) images created by a mechanically or electronically rotating probe (e.g., wobbler) to form a volume. For orthogonal 3D rendering, parallel rays extend through the volume. Data is rendered to a display as a function of the rays. To obtain an aesthetically pleasing volume image, various filtering methods, opacity curves, tint maps and smoothing filtering are provided. Perspective rendering may alternatively be used. The three-dimensional representations are displayed to a user.

Area, distance, volume or other quantitative data may be obtained automatically or manually.

BRIEF SUMMARY

By way of introduction, the preferred embodiments described below include methods, systems and computer readable media for synchronized ultrasound imaging and measurement. Generating three-dimensional representations synchs with measuring one or more parameters. For example, measurements are preformed based on navigating through a volume. The measurements link to the corresponding three-dimensional representations. As another example, the user selects a measurement from a graph. A three-dimensional representation of the volume associated with the selected measurement is presented. Tying the image, such as external or internal views of a cavity, with quantitative data may provide a complete package of the organ in question, helping increase diagnosis confidence and reduce workflow.

In a first aspect, a method synchronizes ultrasound imaging and measurement. A parameter is measured as a function of time, location or time and location. Three-dimensional ultrasound representations, such as a rendering or a multiplanar reconstruction, are synchronized with the time, location or time and location.

In a second aspect, a method synchronizes ultrasound imaging and measurement. A parameter is displayed as a function of time, location or time and location. A selection of a time, location or time and location relative to the display of the parameter is received. A three-dimensional ultrasound representation corresponding to the selected time, location or time and location is generated.

In a third aspect, a method synchronizes ultrasound imaging and measurement. A parameter is displayed as a function of time, location or time and location. A three-dimensional ultrasound representation is displayed. The display of the parameter links to the display of the three-dimensional ultrasound representation.

In a fourth aspect, a computer readable storage medium has stored therein data representing instructions executable by a programmed processor for synchronized ultrasound imaging and measurement. The instructions are for linking virtual endoscopic imaging with quantitative measurement results as a function of fly-through distance, time or fly-through distance and time.

The following claims define the present invention, and nothing in this section should be taken as a limitation on those claims. Further aspects and advantages of the invention are discussed below in conjunction with the preferred embodiments and may be later claimed in combination or independently.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

OB, other GI and/or cardiac imaging use 3D and 4D ultrasound imaging. The imaging allows physicians to view the anatomy. Users also desire quantification for more objective diagnosis of the anatomy. For example, vascular and cardiac applications may rely on one or more measurements for diagnosis. Many treatment plans or the decision whether to use surgical intervention may depend on quantitative criteria, such as the stenosis level and volume ejection fraction. Automatic algorithms may obtain these quantitative measurements.

Virtual endoscopic or 3D imaging links with the quantitative measurements. The measurements are made during or with each rendered volume image. A trace displays the quantitative results, such as vessel cross sectional area, radius/diameter of the vessel cross section, stenosis level, or chamber volume as a function of fly path distance or time. A moving cursor indicates the point on the displayed trace associated with currently displayed 3D representation.

Figure 1:
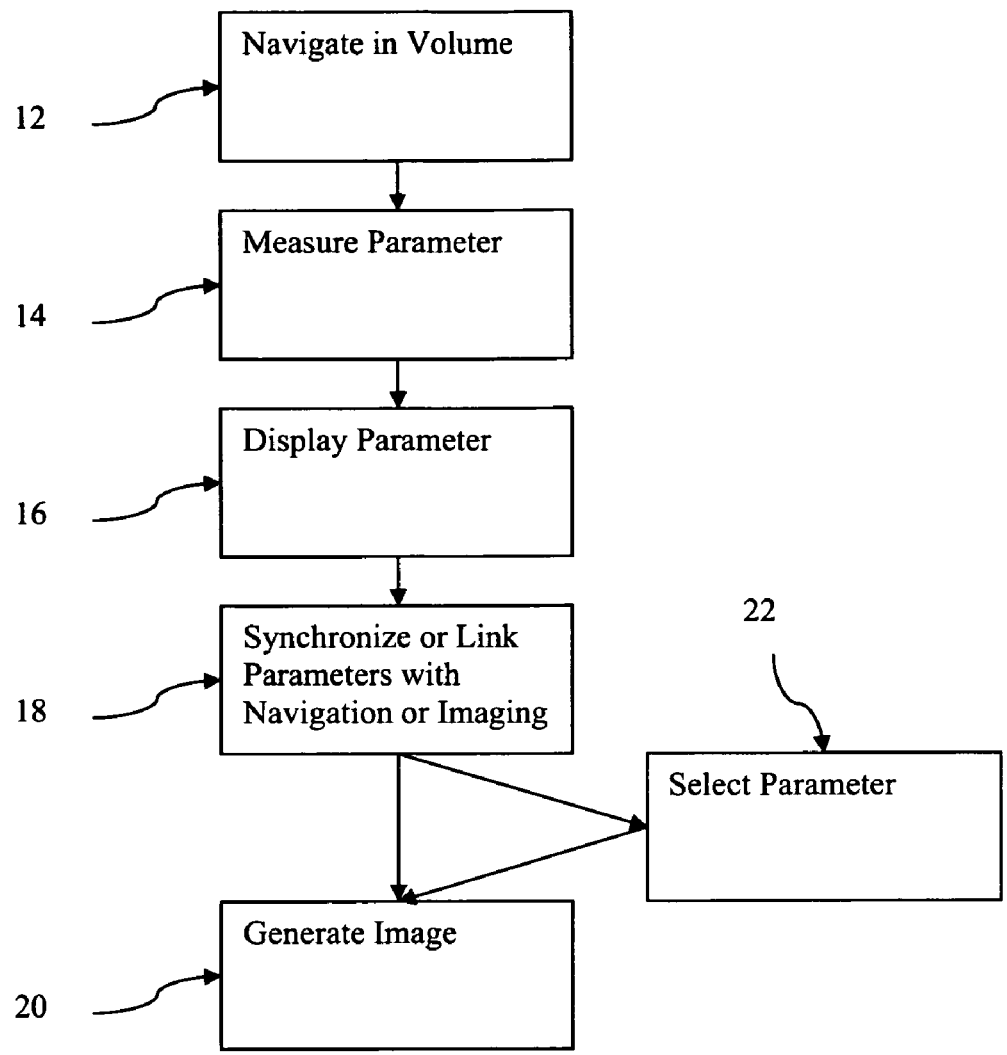
FIG. 1 is a flow chart diagram of one embodiment of a method for synchronizing measurements with three-dimensional imaging.

FIG. 1 shows a method for synchronized ultrasound imaging and measurement. The method uses the systems or instructions described below, but other systems or instructions may be used. The method may provide additional, different or fewer acts. For example, the method operates without acts 16, 20 and/or 22. The method may include linking measurement and image data without displaying the images. The method may include manual or automatic navigation in act 12 and/or selection of parameters in act 22. Other sequences or order of the acts than shown in FIG. 1 may be used.

The method, such as the imaging of acts 16 and/or 20 and the measurements of act 14, are performed with ultrasound data. The ultrasound data is stored representing a volume at one time or real-time ultrasound data representing the volume as a function of time. The method is available to the user during live imaging, during freeze, cine volume, reconstructed cine or recalled 3D/4D volume/volumes from a previous exam, or saved volume/volumes of a current exam. The ultrasound data is B-mode, Doppler flow, Doppler tissue or other ultrasound data representing a region. The ultrasound data is from any stage of ultrasound processing, such as radio frequency, pre-detected, detected, pre-scan converted, or scan converted data. The data represents the region in a polar coordinate format, a regular 3D grid format, a Cartesian coordinate format or both a Cartesian coordinate and polar coordinate (e.g., scan converted 2D frames of data spaced along polar coordinates to represent a volume).

In act 12, a user or processor navigates in a volume. In one embodiment, the navigation, rendering, imaging or other processes disclosed in U.S. application Ser. No. 11/217,211 and U.S. Publication No. 2008/0083099, application Ser. No. 11/241,603, the disclosures of which are incorporated herein by reference, are used. Any now known or later developed navigation tools may be used. For example, the user causes a virtual camera position or viewing location to change within a volume using user controls or a path through a volume. The user may manipulate the image or the virtual camera location and orientation. The movement of the virtual camera is along a straight or curved line or free hand (e.g., any way the user desires). The position may be translated, rotated, zoom or combinations thereof. The user may change the field of view or the depth of the viewing field. The user may flip the camera-viewing window vertically or horizontally, shifting every 90 degrees, or other controls for enhanced workflow.

A graphic or a three-dimensional rendering indicates a current position to the user. For graphics, a dot represents the virtual camera on three two-dimensional images associated with orthogonal planes. The three orthogonal multi-planar renderings intersect at the camera location. Lines extending from the camera representation show the direction at which the camera is pointing, the size of the field of view, and the depth of the viewing field. Other graphics using the same or different renderings may be used. For indicating position based on a three-dimensional rendering, the position of the virtual camera is controlled with respect to perspective or orthogonal three-dimensional rendered medical image. Manual input moves the virtual camera within the scanned volume. The three-dimensional medical image updates or is re-rendered as the position changes, providing feedback to the user.

Automated navigation may be used. A processor positions the camera location based on a path or other parameter. The cameral location may be changed or remain in one location. For example, the processor controls an automatic fly-through of a vessel or chamber.

The navigation operates for a static data set, for a sequence of medical images or for real-time imaging. For example, during a sequence of images for a scanned volume, the camera position stays in a same location between images or data sets as a function of time. The volume changes, such as heart walls contracting and relaxing, while the camera location is static or repositioned to be in a same relative location within the chamber, such as a center of the chamber. As another example, a path is determined manually or automatically along a vessel. The camera location moves at a same rate or varying rate along the path. Yet another example, the user moves the camera location anywhere within the vessel or chamber. Any other now known or later developed virtual endoscopy or "fly through" navigation may be used.

In act 14, a parameter is measured as a function of time, location or time and location. The parameter is a function of time where the ultrasound data representing the volume changes as a function of time, but the measurement location is static. The parameter is a function of location where the measurement location changes position within a static set of ultrasound data. The parameter is a function of time and location where the measurement location changes position and the ultrasound data representing the volume changes as a function of time (e.g., real-time fly through).

The parameter is an area, volume, stenosis level, diameter, derivative thereof, or combinations thereof. The location of measurement is a function of the parameter. For example, area may be a cross-sectional area at the camera or rendering location. For vascular applications, vessel cross sectional area, maximum diameter, minimum diameter, stenosis level and relative volume change are for a region of interest. For cardiac applications, the relative chamber volume change, wall motion reflected as cross sectional area, and their derivatives, such as the ratio of the diastole and systole chamber volumes, are measured as a function of cardiac cycle. For bladder applications, the relative volume change of the internal cavity is measured as the bladder fills up or drained. For neonatal brain ventricle applications, the internal cavity, ventricle volume size is measured. For cysts of any organ, the volume of the cyst is measured. Other now known or later developed parameters may be measured. A single parameter or a combination of two or more parameters is measured.

The measurement is automatic. For example, a processor identifies a border from the ultrasound data. The border is the same or different than any surface used for rendering three-dimensional representations. A threshold, gradient, line or surface tracking, or other image process identifies the border. In one embodiment, the border is determined using the methods or systems of U.S. Pat. Nos. 6,606,091 or 6,771,262, the disclosures of which are incorporated herein by reference. User assisted measurements may be used. For example, the user indicates one or more locations along a border. The processor uses the locations to identify the entire border. As another example, the processor estimates a border location. In response to user correction of one or more points along the estimated border, the processor refines the border estimation. Alternatively, the measurement is manual. For example, the user traces an area or indicates an approximate volume boundary.

For stenosis, the amount of blockage is calculated. The amount of blockage is a function of a ratio of the cross-sectional flow area to a cross-sectional vessel area. Alternatively, an area of plaque may be used. Using thresholds, pattern recognition, Doppler flow or other process, the vessel wall is distinguished from plaque within the vessel by the processor or the user.

The location of the measurements is based on the navigation in one embodiment. The parameter is measured during the fly-through as a function of the navigating. As the user or the system navigates manually or automatically through a volume, the parameter is measured. The navigation is the same or different navigation used for three-dimensional rendering. For example, the virtual camera is still or has a static location inside a cavity, such as a heart chamber, bladder, gallbladder, brain ventricle, ovary, uterus or a vessel. The cross sectional area or diameter coincides with the camera location. A largest, smallest or other cross-section area associated with the volume or cavity at the location is obtained. The volume is the entire volume for a closed cavity, such as a heart chamber or a partial volume of a vessel with a user specified region of interest. For example, the volume of a heart chamber is cropped at the valves so that volume of other chambers is not included in any area or volume measurements.

In act 16, the parameter is displayed as a function of the time, location or time and location. The parameter is a quantity, such as a table of measured values at different times or locations. Alternatively, the parameter is in a graphic, such as a graph with parameter values. The graphic represents measurements associated with the automatic or manual fly-through path. The displayed trace is either built up during the fly-through or shown over a selected length or time, such as over a user selected length or time.

Figure 3A:
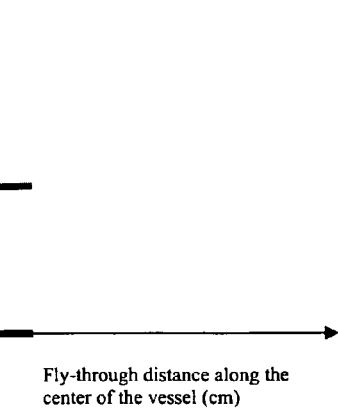
FIGS. 3A-C are example graphical representations of parameters displayed in conjunction with the representations of FIGS. 2A-C, respectively.
Figure 3B:
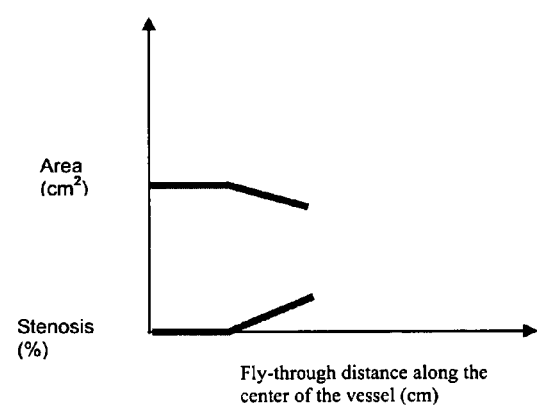
Figure 3C:
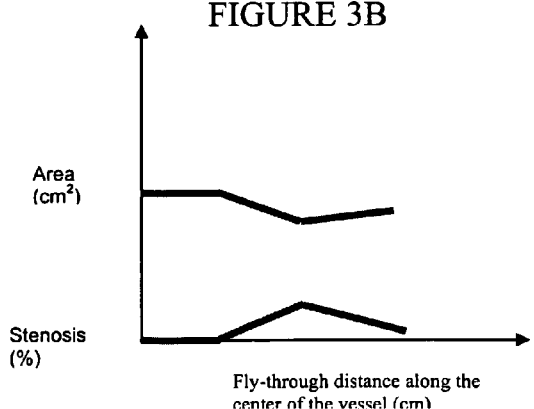

FIGS. 3A-C show the area and stenosis as a function of location along the fly path. FIG. 3A shows the area and stenosis along a vessel prior to a branch. FIG. 3B shows the area and stenosis of FIG. 3A with additional measurements near a branch location. FIG. 3C shows the area and stenosis of FIG. 3B with additional measurements along a selected branch. FIGS. 3A-C represent a sampling of sequential displays. Alternatively, the graphic is first generated to include parameter values for the entire path.

Figure 5A:
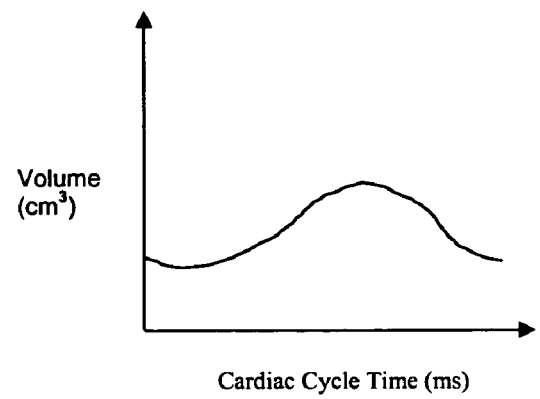
FIGS. 5A-C are example graphical representations of parameters displayed in conjunction with the representations of FIGS. 4A-C, respectively.
Figure 5B:
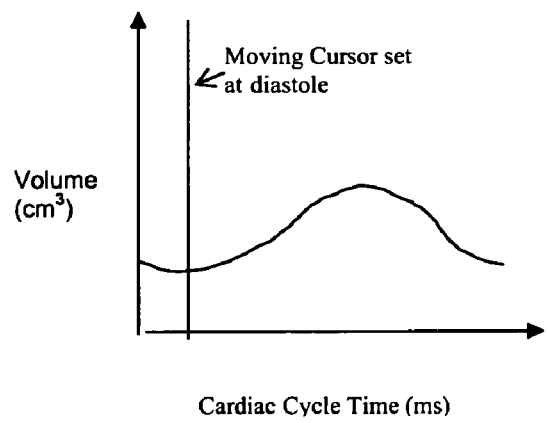
Figure 5C:
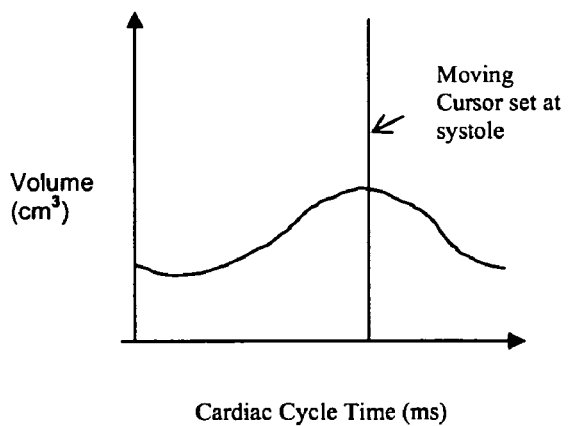

FIGS. 5A-C show the volume of a left ventricle as a function of time. The volume graph is the same in each of FIGS. 5A-C and represents the volume throughout a heart cycle. FIG. 5B shows a cursor or line at diastole. FIG. 5C shows the cursor or line at systole. In alternative embodiments, the graph provides the volume or other parameter as the parameters are measured, ending the graph at the cursor or line.

In act 18, the parameters are linked or synchronized with the navigation or imaging. For example, the navigation synchronizes with the measured parameters. The user manually guides generation of three-dimensional representations through navigation. The parameters are measured as the three-dimensional ultrasound representations are generated. The measurements are more intuitive, quicker and easier to obtain, and may be obtained with or without user activation during the navigation. In the embodiments shown in FIGS. 3A-C, the cross sectional area and stenosis level synchronize with the virtual camera location during the fly-through. The fly-through is either automatic or manual.

Where the navigation corresponds to imaging, the measurements of the parameters link to the imaging. For example, three-dimensional ultrasound representations synchronize as a function of the time, location or time and location of the parameter measurements. The display of the parameters links to the display of the three-dimensional ultrasound representation. For example, a virtual endoscopic imaging links with quantitative measurement results as a function of fly-through distance, time or fly-through distance and time. Quantitative measurement results obtained from a volume are displayed as traces or other graphical or text presentations versus time or geometrical location and correspond to the associated three-dimensional representation.

Synchronization or linking associates the view of the cavity or volume with the measurement data. As the images of the volume are generated, the measurements for corresponding locations are made. The clinicians obtain relevant information simultaneously and intuitively as images and measurements, possibly aiding diagnosis, surgical planning and/or treatment planning. The linking provides a mechanism to associate the measurements with viewed structure, allowing more efficient communication between physician and patient, among physicians and for training.

In act 20, at least one three-dimensional representation is generated and displayed. Three-dimensional representations represent the volume. Three-dimensional rendering, such as orthogonal or perspective rendering, represent the volume from a selected viewing direction and/or location. Minimum, maximum, average or other projection, alpha blending or other rendering is used. Shading, opacity control, or other now known or later developed volume rendering effects may be used. Alternatively, surface rendering is provided.

Another three-dimensional representation is multiplanar reconstruction. Two or more two-dimensional images at different locations in the volume are rendered substantially simultaneously. For example, three orthogonal planes intersect at the navigation or camera location. Three two-dimensional images represent the volume. As the virtual camera changes locations or alters position, the location of the planes within the scanned volume changes to maintain the intersection throughout movement of the virtual camera. The update rate of plane positions is the same or different from the update rate of positioning of the virtual camera. One or more planes and associated images not intersecting the current position of the virtual cameral may be provided.

Figure 2A:
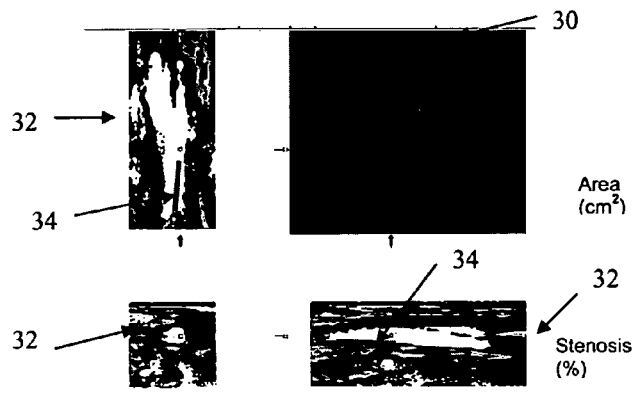
FIGS. 2A-C are example graphical representations of a sequence of three-dimensional representations at different locations.
Figure 2B:
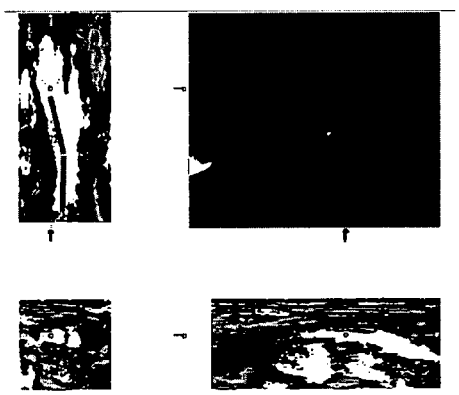
Figure 2C:
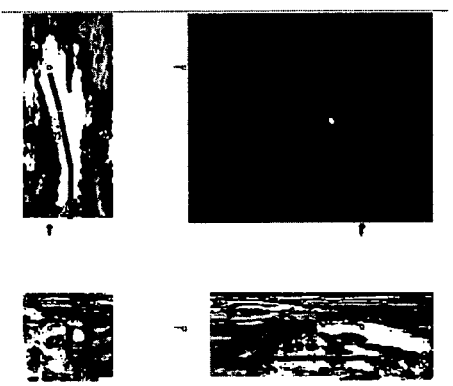
Figure 4A:
FIGS. 4A-C are example graphical representations of a sequence of three-dimensional representations at different times.
Figure 4B:
Figure 4C:
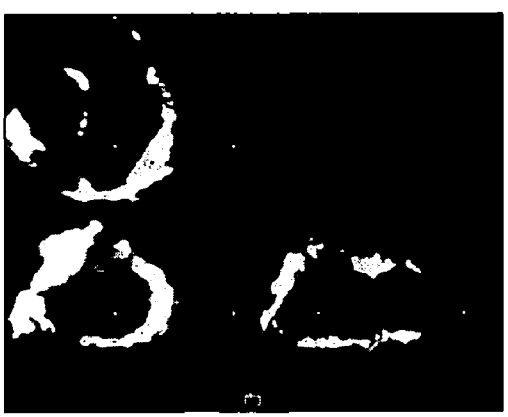

One or more three-dimensional representations are displayed substantially simultaneously. FIGS. 2A-C and 4A-C show two embodiments displaying three-dimensional representations. FIG. 2A shows a perspective rendering 30 and a multiplanar reconstruction 32. Optional graphics may overlay the images, such as indicating a navigation path 34 on the multiplanar reconstruction 32. The navigation path 34 corresponds to previous and current locations of navigation. FIGS. 2B and 2C show the same volume rendered for different locations. FIGS. 4A-C shows three-dimensional representations at different times.

The two-dimensional image or images 32 are displayed substantially simultaneously with the three-dimensional rendering image 30. The update or refresh rate of the different images may be different, but the user sees the images at generally a same time. In one embodiment, the multiplanar reconstructions 32 are displayed at a same time as the three-dimensional perspective rendered image 30. The multiplanar reconstructions 32 and perspective rendering 30 are oriented relative to each other.

One or more of the three-dimensional representations may include a graphic indicating a current location. For example, the images of the multiplanar reconstruction 32 include a representation of the position of the virtual camera. One, more, or all of the two-dimensional images include the representation. Any representation may be used, such as a dot. A camera icon, an intersection of lines, an arrow or other representation may be used. The representation indicates the position to the user. The representation includes or does not include additional graphics in other embodiments. For example, dashed lines or a shaded field represents the field of view.

Additional three-dimensional ultrasound representations are generated as a function of navigation within the volume. A sequence of three-dimensional representations is displayed as a function of time, location or time and location. For example, a static set of data represents a scanned volume. As the user navigates, repositioning the virtual camera into different locations, different renderings result. FIGS. 2A-C show three-dimensional representations for different locations within a vessel. As another example, different renderings result from different data sets with or without repositioning the virtual camera. The renderings result from imaging a sequence. FIGS. 4A-C show three-dimensional representations for different times during a heart cycle. FIG. 4A corresponds to imaging a left ventricle when viewed from inside looking up towards a mitral valve at the time of the valve opening. FIG. 4B corresponds to imaging at diastole. FIG. 4C corresponds to imaging at systole.

The three-dimensional ultrasound representations are each associated with a measurement of the parameter. Parameter values correspond to respective ones of the three-dimensional representations. For example, the displays of FIGS. 2A-C are on a same display screen with the displays of FIGS. 3A-C, respectively. As the three-dimensional representations are generated, such as due to navigation through the volume, synchronous measurements are performed or indicated from previously performed measurements. The three-dimensional ultrasound representations correspond to particular parameter values as a function of location, time or location and time. In the examples of FIGS. 2 and 3, the graph of parameter values ends at a current location represented by the currently displayed three-dimensional representations. As the user or processor navigates in a fly-through of an at least partially enclosed structure, the three-dimensional ultrasound representations are rendered, and linked measurements are performed during the fly-through.

In an alternative embodiment, the parameter values are linked or synchronized with the three-dimensional representations in the display after or during navigation. FIGS. 5A-C each show the parameter values over a heart cycle. The parameter values are previously measured or are measured as navigation occurs. As different three-dimensional representations are generated during navigation, the linked or synchronized parameter value is highlighted. For example, a color, line or other graphic indicates a location, time or location and time on the display of the parameter. The indication corresponds to the currently displayed three-dimensional ultrasound representation associated with the highlighted location, time or location and time.

Synchronizing the imaging and measurements during navigation may assist in diagnosis by the user. Synchronizing the imaging and measurements may assist alternatively or additionally with navigation. In act 22 of FIG. 1, a parameter value is selected. The selection is manual, such as receiving a selected time, location or time and location. Referring to FIGS. 5B and 5C, the user clicks on the graph or positions the bar along the graph of parameter values displayed as a function of time. Alternatively, the selection is automatic. For example, a processor determines a time, location or time and location associated with a minimum, maximum, mean, or other characteristic of the parameter values.

One or more linked three-dimensional ultrasound representations are displayed in act 20 in response to the selection of act 22 based on the synchronization of act 18. The three-dimensional ultrasound representation corresponds to the selected time, location or time and location. As different parameter values are selected, related or linked three-dimensional representations are displayed. For example, the user or processor slides the cursor or bar on the graph of parameter values. The displayed three-dimensional representations change in synchronization with the cursor change in position.

Figure 6:
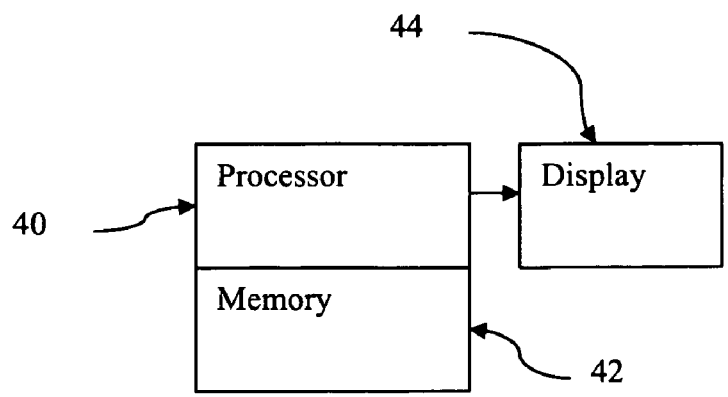
FIG. 6 is a block diagram of one embodiment of a system and computer readable media for synchronized ultrasound imaging and measurement.

FIG. 6 shows one embodiment of a system for synchronized ultrasound imaging and measurement. The system implements the method of FIG. 1 or other methods. The system is a medical ultrasound acquisition and imaging system, such as cart based, portable or handheld ultrasound system. Other medical acquisition systems may be used, such as computed tomography, magnetic resonance, positron emission or other imaging systems. In alternative embodiments, the system is a computer, personal computer, laptop, DICOM workstation or other workstation. For example, a desktop application processes medical data or ultrasound volumes offline. The offline-processing unit receives ultrasound 3D or 4D volumes. Offline volume processing software manipulates the volume for navigation and rendering as discussed herein. The system may include additional, different or fewer components. For example, a user input, such as a 3D joystick, keyboard, mouse, trackball, or similar device, is provided for manual control of navigation or selection of parameter values. As another example, a network connection is provided for remote manipulation of the system, remote navigation or remote selection.

The processor 40 is a control processor, general processor, digital signal processor, application specific integrated circuit, field programmable gate array, network, server, group of processors, data path, combinations thereof or other now known or later developed device for synchronizing imaging and measurement. For example, the processor 40 as a single component or a plurality of separate components (e.g., network or group of processors) measures one or more parameters, generates displays and synchronizes the parameters with three-dimensional imaging. The processor 40 operates pursuant to instructions stored in the memory 42 or another memory. The processor 40 is programmed for synchronizing measurement, three-dimensional imaging, parameter display and navigation.

A memory 42 stores the data sets representing the scanned volume and/or instructions for implementing the synchronization, rendering, measurements, displays and/or navigation. The memory 42 is a computer readable storage medium having stored therein data representing instructions executable by the programmed processor 40 for synchronizing measurements and imaging. The instructions implement the processes, methods and/or techniques discussed herein. The memory 42 is a computer-readable storage media or memory, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 42 may store alternatively or additionally medical image data for generating images. The medical data is ultrasound, MRI, CT or other medical imaging data. The medical data is of display values or data prior to mapping for display.

The display 44 is a CRT, LCD, projector, plasma, or other display for displaying three-dimensional representations, graphics, numerical values, combinations thereof or other information. The display 44 receives parameter values or graphics from the processor 40. The display 44 shows images of the graphics, parameter values and/or three-dimensional representations. The 3D image may be displayed as a monoscopic or stereoscopic image by a variety of means, such as shutter glasses, autostereo panel, polarized glasses or hologram.

While the invention has been described above by reference to various embodiments, it should be understood that many changes and modifications could be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for synchronized ultrasound imaging and measurement, the storage medium comprising instructions for:
measuring, from ultrasound data, a parameter as a function of location, the measuring providing values of the parameter for different locations;
synchronizing three-dimensional ultrasound representations with the location associated with the measured parameter such that one of the three-dimensional representations is provided for each of the values and rendered from the corresponding ultrasound data and location for the value; and
displaying the measured parameter as quantities or a graph associated with the locations, the graph comprising a displayed value axis representing an increasing range of possible values and a displayed location axis where the values are plotted along the location and value axes, and the quantities comprising numbers or text;
wherein synchronizing comprises generating the three-dimensional ultrasound representations associated with the measured parameter by navigating in a fly-through of an at least partially enclosed structure and rendering the three-dimensional ultrasound representations during the fly-through, the fly-through comprising rendering from different perspective locations within the at least partially enclosed structure such that a sequence provided by the three-dimensional ultrasound representations uses the different perspective locations and simulates moving through the at least partially enclosed structure, and wherein the measured parameter is measured during the fly-through as a function of the navigating.

2. The non-transitory computer readable storage medium of claim 1 wherein synchronizing comprises measuring the parameter linked to navigating through a volume for generating the three-dimensional representations.

3. The non-transitory computer readable storage medium of claim 1 wherein measuring the parameter comprises measuring the parameter as a function of time.

4. The non-transitory computer readable storage medium of claim 1 wherein measuring the parameter comprises measuring the parameter as a function of location.

5. The non-transitory computer readable storage medium of claim 1 wherein the synchronizing of the three-dimensional representations comprises synchronizing the three-dimensional representations as multiplanar reconstructions, three-dimensional renderings, or multiplanar reconstructions and three-dimensional renderings.

6. The non-transitory computer readable storage medium of claim 1 wherein the synchronizing of the three-dimensional representations comprises synchronizing the three-dimensional representations as orthogonal or perspective renderings.

7. The non-transitory computer readable storage medium of claim 1 further comprising:
receiving a selection of location; and
generating at least one of the three-dimensional representations as a function of the selection.

8. The non-transitory computer readable storage medium of claim 1 wherein measuring from ultrasound data comprises calculating an area, a volume, a stenosis level, a diameter, a derivative thereof, or combinations thereof.

9. In a non-transitory computer readable storage medium having stored therein data representing instructions executable by a programmed processor for synchronized ultrasound imaging and measurement, the storage medium comprising instructions for:
displaying a parameter from ultrasound data as a function of time, location or time and location, the displaying comprising displaying a graph with a displayed value axis representing an increasing range of possible values of the parameter and a displayed location or time axis where values of the parameter are plotted along the location or time and value axes;
receiving a selection on the graph of a time, location or time and location relative to the display of the parameter; and
generating a three-dimensional ultrasound representation corresponding to the selected time, location or time and location.

10. The non-transitory computer readable storage medium of claim 9 further comprising:
generating an additional three-dimensional ultrasound representation as a function of navigation within a volume;
measuring the parameter as function of the navigation in the volume; and
synchronizing the navigation with the measured parameters.

11. The non-transitory computer readable storage medium of claim 10 wherein synchronizing the navigation comprises measuring the parameters as the plurality of three-dimensional ultrasound representations is generated.

12. In a non-transitory computer readable storage medium having stored therein data representing instructions executable by a programmed processor for synchronized ultrasound imaging and measurement, the storage medium comprising instructions for:
acquiring ultrasound data representing anatomy;
displaying a graph or a table including a parameter from the ultrasound data as a function of time, location or time and location, the graph or table having a first axis labeled as a parameter axis and a second axis labeled as a time or location axis and having values of the parameter plotted along the first and second axes;
displaying a three-dimensional ultrasound representation of the anatomy with the ultrasound data; and
linking the display of the parameter to the display of the three-dimensional ultrasound representation such that selection of a time or location on the graph or table controls the three-dimensional ultrasound representation being displayed.

13. The non-transitory computer readable storage medium of claim 12 wherein displaying the three-dimensional ultrasound representation comprises displaying a multiplanar reconstruction, an orthogonal rendering, a perspective rendering or combinations thereof.

14. The non-transitory computer readable storage medium of claim 12 wherein linking comprises highlighting a location, time or location and time on the display of the parameter and the three-dimensional ultrasound representation associated with the highlighted location, time or location and time.

15. The non-transitory computer readable storage medium of claim 12 wherein displaying the three-dimensional ultrasound representation comprises displaying a sequence of three-dimensional representations as a function of time, location or time and location, and wherein linking comprises generating the parameter values corresponding to respective ones of the three-dimensional representations.

16. The non-transitory computer readable storage medium of claim 12 wherein linking comprises associating the three-dimensional ultrasound representation with a particular parameter value as a function of location, time or location and time, and wherein displaying the three-dimensional ultrasound representation comprises displaying the three-dimensional ultrasound representation associated with a selected time, location or location and time.

17. In a non-transitory computer readable storage medium having stored therein data representing instructions executable by a programmed processor for synchronized ultrasound imaging and measurement, the storage medium comprising instructions for:
providing ultrasound data representing anatomy;
linking virtual endoscopic imaging with quantitative measurement results as a function of fly-through distance, time or fly-through distance and time; and
displaying the quantitative measurement results as a function of fly-through distance, time or fly-through distance and time as the renderings are performed for the corresponding fly-through distance, time or fly-through distance and time, the linking providing for simultaneous display of the quantitative measurement results with the imaging for the same fly-through distance, time or fly-through distance and time, the quantitative measurement results displayed as a graph or table having a first axis labeled as a parameter axis and a second axis labeled as a time or location axis and having values of the parameter plotted along the first and second axes.

18. The non-transitory computer readable storage medium having instructions of claim 17 wherein the linking with the virtual endoscopic imaging comprises linking with, as the virtual endoscopic imaging, orthogonal or perspective rendering of the ultrasound data representing a volume.

19. The non-transitory computer readable storage medium having instructions of claim 17 wherein the linking comprising linking the virtual endoscopic imaging with the quantitative measurement results, the virtual endoscopic imaging and the quantitative measurement results being derived from the ultrasound data, the ultrasound data comprising stored or real-time ultrasound data representing a volume at one time or a volume as a function of time.

\* \* \* \* \*